United States Patent
Petersik et al.

(10) Patent No.: US 12,310,636 B2
(45) Date of Patent: ***May 27, 2025

(54) FEMORAL NAIL WITH ENHANCED BONE CONFORMING GEOMETRY

(71) Applicant: Stryker European Operations Holdings LLC, Kalamazoo, MI (US)

(72) Inventors: Andreas Petersik, Heikendorf (DE); Hendrik Kluever, Schoenkirchen (DE); Giovanni Ricciardi, Munich (DE)

(73) Assignee: Stryker European Operations Holdings LLC, Portage, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/216,803

(22) Filed: Jun. 30, 2023

(65) Prior Publication Data

US 2023/0338069 A1 Oct. 26, 2023

Related U.S. Application Data

(63) Continuation of application No. 17/228,806, filed on Apr. 13, 2021, now Pat. No. 11,730,525, which is a continuation of application No. 16/381,453, filed on Apr. 11, 2019, now Pat. No. 11,013,540.

(60) Provisional application No. 62/657,279, filed on Apr. 13, 2018.

(51) Int. Cl.
*A61B 17/72* (2006.01)
*A61B 17/92* (2006.01)

(52) U.S. Cl.
CPC ...... *A61B 17/7283* (2013.01); *A61B 17/7233* (2013.01); *A61B 17/921* (2013.01)

(58) Field of Classification Search
CPC ............ A61B 17/7241; A61B 17/7283; A61B 17/7233; A61B 17/72
See application file for complete search history.

(56) References Cited

U.S. PATENT DOCUMENTS

| | | | |
|---|---|---|---|
| 3,709,218 A | 1/1973 | Halloran | |
| 4,133,507 A | 1/1979 | Chervenak | |
| 4,135,507 A * | 1/1979 | Harris | A61B 17/7208 606/62 |
| 4,475,545 A | 10/1984 | Ender | |

(Continued)

FOREIGN PATENT DOCUMENTS

| | | |
|---|---|---|
| AU | 2014338523 A1 | 6/2016 |
| EP | 0257118 A1 | 3/1988 |

(Continued)

OTHER PUBLICATIONS

Extended European Search Report issued in Appln. No. 23208201.6 dated Jan. 23, 2024 (8 pages).

(Continued)

*Primary Examiner* — Julianna N Harvey
(74) *Attorney, Agent, or Firm* — Lerner David LLP (57) ABSTRACT

A femoral nail includes a proximal section, a distal section remote from the proximal section, and an intermediate section disposed between the proximal section and distal section and having first and second curved portions. The first curved portion is positioned closer to the proximal section than the second curved portion. The second curved portion is curved in a first plane, and the first curved portion is curved in the first plane and a second and third plane.

20 Claims, 7 Drawing Sheets

(56) References Cited

U.S. PATENT DOCUMENTS

| | | |
|---|---|---|
| 4,919,673 A | 4/1990 | Willert et al. |
| 5,041,115 A | 8/1991 | Frigg et al. |
| 5,066,296 A | 11/1991 | Chapman et al. |
| 5,176,681 A | 1/1993 | Lawes et al. |
| 5,454,813 A | 10/1995 | Lawes |
| 6,010,505 A | 1/2000 | Asche et al. |
| 6,010,506 A | 1/2000 | Gosney et al. |
| 6,120,504 A | 9/2000 | Brumback et al. |
| 6,210,414 B1 | 4/2001 | Lin et al. |
| 6,461,360 B1 | 10/2002 | Adam |
| 6,702,816 B2 | 3/2004 | Buhler |
| 6,855,146 B2 | 2/2005 | Frigg et al. |
| 7,670,340 B2 | 3/2010 | Brivio et al. |
| 7,947,043 B2 | 5/2011 | Mutchler |
| 8,317,788 B2 | 11/2012 | Kaup |
| 8,790,343 B2* | 7/2014 | Mcclellan ........... A61B 17/7241 606/65 |
| 8,906,024 B2* | 12/2014 | Schlienger ............. A61B 17/72 606/64 |
| 11,013,540 B2* | 5/2021 | Petersik ............. A61B 17/7283 |
| 11,253,298 B2 | 2/2022 | Prien et al. |
| 11,730,525 B2* | 8/2023 | Petersik ................. A61B 17/72 606/64 |
| 2002/0099379 A1* | 7/2002 | Adam .................... A61B 17/72 606/67 |
| 2002/0183750 A1 | 12/2002 | Buhler |
| 2007/0123873 A1* | 5/2007 | Czartoski ........... A61B 17/7233 606/62 |
| 2007/0123874 A1 | 5/2007 | Czartoski et al. |
| 2008/0009869 A1* | 1/2008 | Schlienger ............. A61B 17/72 606/64 |
| 2011/0282347 A1* | 11/2011 | Gordon .................. A61B 17/72 606/104 |
| 2012/0163683 A1 | 6/2012 | Wilson et al. |

FOREIGN PATENT DOCUMENTS

| | | |
|---|---|---|
| JP | 2012130724 A | 7/2012 |
| JP | 2012-531995 A | 12/2012 |
| RU | 2271768 C1 | 3/2006 |
| WO | 0071040 A1 | 11/2000 |
| WO | 2011002903 A2 | 1/2011 |
| WO | 2013090859 A1 | 6/2013 |
| WO | 2021/176272 A1 | 9/2021 |
| WO | 2021/176274 A1 | 9/2021 |

OTHER PUBLICATIONS

Extended European Search Report including the Written Opinion for Application No. EP 19168725.0 dated Sep. 3, 2019, 8 pages.
Stryker, "Gamma3® Hip Fracture Nailing System Operative technique", Stryker Trauma GmbH (2022). 68 pgs.

* cited by examiner

FEMORAL NAIL WITH ENHANCED BONE CONFORMING GEOMETRY

CROSS-REFERENCE TO RELATED APPLICATIONS

The present application is a continuation of U.S. patent application Ser. No. 17/228,806, filed Apr. 13, 2021, which is a continuation of U.S. patent application Ser. No. 16/381,453, filed Apr. 11, 2019, which claims the benefit of the filing date of U.S. Provisional Patent Application No. 62/657,279, filed on Apr. 13, 2018, all of which are incorporated herein by reference.

BACKGROUND OF THE INVENTION

The skeletal system includes several long bones including the femur. The femur is the longest of the long bones and is generally divided into three regions: the proximal femur, distal femur, and femoral shaft. Femoral fractures, which are commonly caused by acute trauma, can occur at or between any one of these regions. Such fractures often require internal devices to reduce and immobilize the fractured bone.

One such device is a femoral, intramedullary nail. Femoral nails are elongate structures that are inserted into an intramedullary canal through either the proximal femur or distal femur. Such nails are typically bent along their respective lengths in an attempt to follow the natural curvature of a human long bone, such as the anterior bow found in virtually all human femurs.

However, since anatomy varies from patient to patient, it has been difficult to develop appropriate femoral nail geometries that are suitable for the entire patient population. This difficulty has been confirmed by recent database analyses of femurs that have found that certain curvatures of the human femur are greater than originally considered. In this regard, current femoral nails are generally disproportionately curved relative to the femurs into which they are implanted. This disproportionality may result in impingement of the femoral cortex during implantation potentially resulting in fracture and also malalignment of the femoral nail which can be uncomfortable for the patient and result in less than desirable outcomes. Therefore, further improvements are desirable.

BRIEF SUMMARY OF THE INVENTION

A femoral nail is disclosed that includes a proximal section, a distal section, and an intermediate section. The proximal and distal sections extend along their own axes and are substantially straight. The intermediate section is disposed between the proximal section and distal section and includes a first curved portion, a straight portion, and a second curved portion. The straight portion is disposed between the first and second curved portions. The second curved portion is curved in a first plane and has a radius that substantially matches a radius of an anterior bow of a patient's femur as may be approximated based upon a database population analysis. The first curved portion is curved in the first plane and also in a second and third plane. The second plane intersects the first plane at an oblique angle, and the third plane is a resultant of this oblique angle and the magnitude of the bends of the nail in the first and second planes. Such multiplane curvature has been determined by database analysis to provide optimal fit for the general patient population and to reduce incidence of femoral cortex impingement.

In one aspect of the present disclosure, a femoral nail includes a proximal portion configured to engage a driving tool for driving the femoral nail into a femur, a distal portion remote from the proximal portion, and an intermediate portion disposed between the proximal end and distal end. The intermediate portion includes a plurality of bends such that a first bend is in a first plane, a second bend is in a second plane, and a third bend is in a third plane. The first and second planes intersect at an oblique angle relative to each other. The third bend is a resultant of the first and second bends and has a magnitude greater than the first and second bends.

Additionally, the distal end may be straight and may include a plurality of through-holes extending through the distal end in a direction transverse to a distal end axis. The first plane may be greater than 80 degrees and smaller than 120 degrees relative to the second plane. In one example, the first plane is preferably 100 degrees relative to the second plane. The first plane may extend in an anterior-posterior direction, and the second plane may extend substantially in a medial-lateral direction.

Continuing with this aspect, the first bend may be 3 degrees, the second bend may be 4 degrees, and the third bend may be greater than 4 degrees. The intermediate portion may have a radius of curvature in the first plane. Also, the proximal end of the femoral nail may include a plurality of through-holes extending therethrough. At least a first and second through-hole of the plurality of through-holes may have respective first and second through-hole axes that lay in the second plane. Furthermore, the proximal end may include at least one rotational alignment characteristic for indicating a rotational alignment of the femoral nail relative to a femur. The rotational alignment characteristic may be rotationally offset from the third plane by an acute angle. The acute angle may be less than 50 degrees. The rotational alignment characteristic may be an engagement notch configured to engage the driving tool. Also, the third plane may intersect the second plane at an acute angle less than 50 degrees. Each of the bends may be an equal distance from a terminal end of the proximal portion.

In another aspect of the present disclosure, a femoral nail includes a proximal section that has a longitudinal axis extending along its length, a distal section remote from the proximal section, and an intermediate section disposed between the proximal section and distal section. The intermediate section has a straight portion and first bent portion. The first bent portion is disposed between the straight portion and the proximal section. The first bent portion is bent in first, second, and third planes such that a longitudinal axis of the straight portion is oriented relative to a longitudinal axis of the proximal section by first, second, and third angles within the respective first, second, and third planes, and wherein the first, second, and third angles differ from one another.

Additionally, the intermediate section may also include a second bent portion disposed between the straight portion and distal section. The second bent portion may be bent in the first plane. The second bent portion may have a radius of curvature of 500-1500 mm. The proximal and distal sections may be straight along their respective lengths. The magnitude of the third angle may be a resultant of the respective magnitudes of the first and second angles and the orientation of the first and second planes relative to each other. The first angle may be 3 degrees, the second angle may be 4 degrees, and the third angle may be more than 4 degrees. The first plane may be greater than 80 degrees and smaller than 120 degrees relative to the second plane. The proximal section may include a first screw hole configured to direct a bone screw toward a femoral head when implanted within a femur. The bone screw hole may define a screw hole axis lying in the second plane. The distal section may include a second screw hole extending therethrough and defining screw hole axis lying in the second plane.

In a further aspect of the present disclosure, a femoral nail includes a proximal section, a distal section remote from the proximal section, and an intermediate section disposed between the proximal section and distal section. The intermediate section includes first and second curved portions. The first curved portion is positioned closer to the proximal section than the second curved portion. The second curved portion is curved in a first plane, and the first curved portion is curved in the first plane and a second and third plane.

Additionally, the second curved portion may be curved in the first plane and only in the first plane. The distal section may extend from the second curved portion and terminate at a distal tip. Also, the first and second planes may be oriented relative to each other at an obtuse angle, and the third plane may be disposed between the first and second planes and may be oriented relative to the first plane at an acute angle.

In an even further aspect of the present disclosure, a femoral nail includes a first section having a first screw hole extending through a sidewall thereof and defining a screw hole axis configured to extend toward a femoral head when the femoral nail is implanted within a femur. The screw hole axis lies in a first plane, and a second section extends from the first section and has first and second curved portions. The first curved portion is positioned closer to the first section than the second curved portion. The first curved portion is curved in the first plane and a second and third plane. The first curved portion has a proximal-distal length greater than that of the first curved portion.

Additionally, the second curved portion may terminate at a distal tip of the femoral nail. The nail may also include a distal section extending from the second curved portion. The second curved portion may be curved in the second plane. The first and second planes may be oriented relative to each other at an obtuse angle, and the third plane may be disposed between the first and second planes and may be oriented relative to the second plane at an acute angle.

BRIEF DESCRIPTION OF THE DRAWINGS

The features, aspects, and advantages of the present invention will become better understood with regard to the following description, appended claims, and accompanying drawings in which:

DETAILED DESCRIPTION

When referring to specific directions in the following discussion of certain implantable devices, it should be understood that such directions are described with regard to the implantable device's orientation and position during exemplary application to the human body. Thus, as used herein, the term "proximal" means close to the heart and the term "distal" means more distant from the heart. The term "inferior" means toward the feet and the term "superior" means toward the head. The term "anterior" means toward the front of the body or the face and the term "posterior" means toward the back of the body. The term "medial" means toward the midline of the body and the term "lateral" means away from the midline of the body. Also, as used herein, the terms "about," "generally" and "substantially" are intended to mean that slight deviations from absolute are included within the scope of the term so modified.

Figure 10:
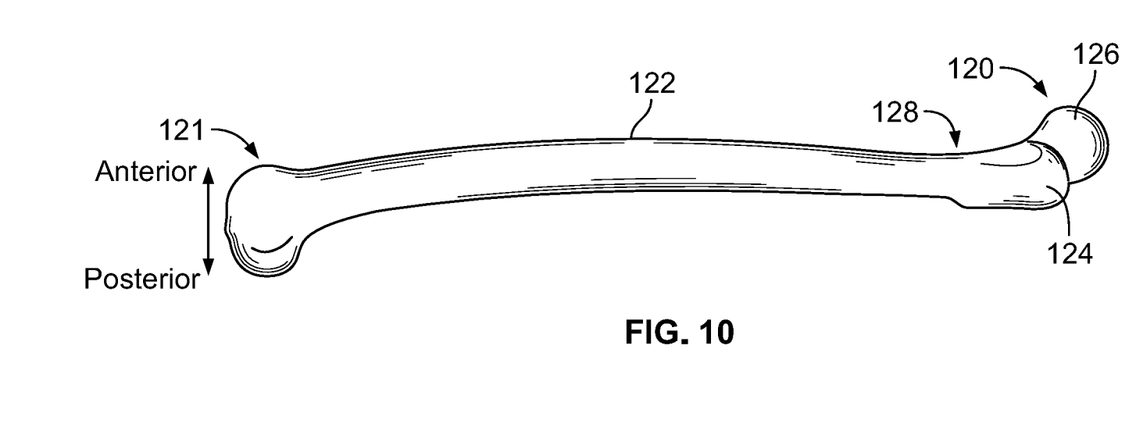
FIG. 10 is a lateral view of a left leg femur.

FIG. 10 depicts an exemplary left leg femur. The femur has a proximal femur 120, distal femur 121, and femoral shaft 122 that extends between the proximal and distal femurs 120, 121. Proximal femur 120 includes a greater trochanter 124 and femoral head 126. As can be seen in FIG. 10, femoral shaft 122 has an anterior bow such that the femur curves anteriorly in an anteroposterior extending plane. However, such curvature does not extend into proximal femur 120 which results in a slight posterior curvature or transitional bend 128 where femoral shaft 122 and proximal femur join 120.

Figure 1:
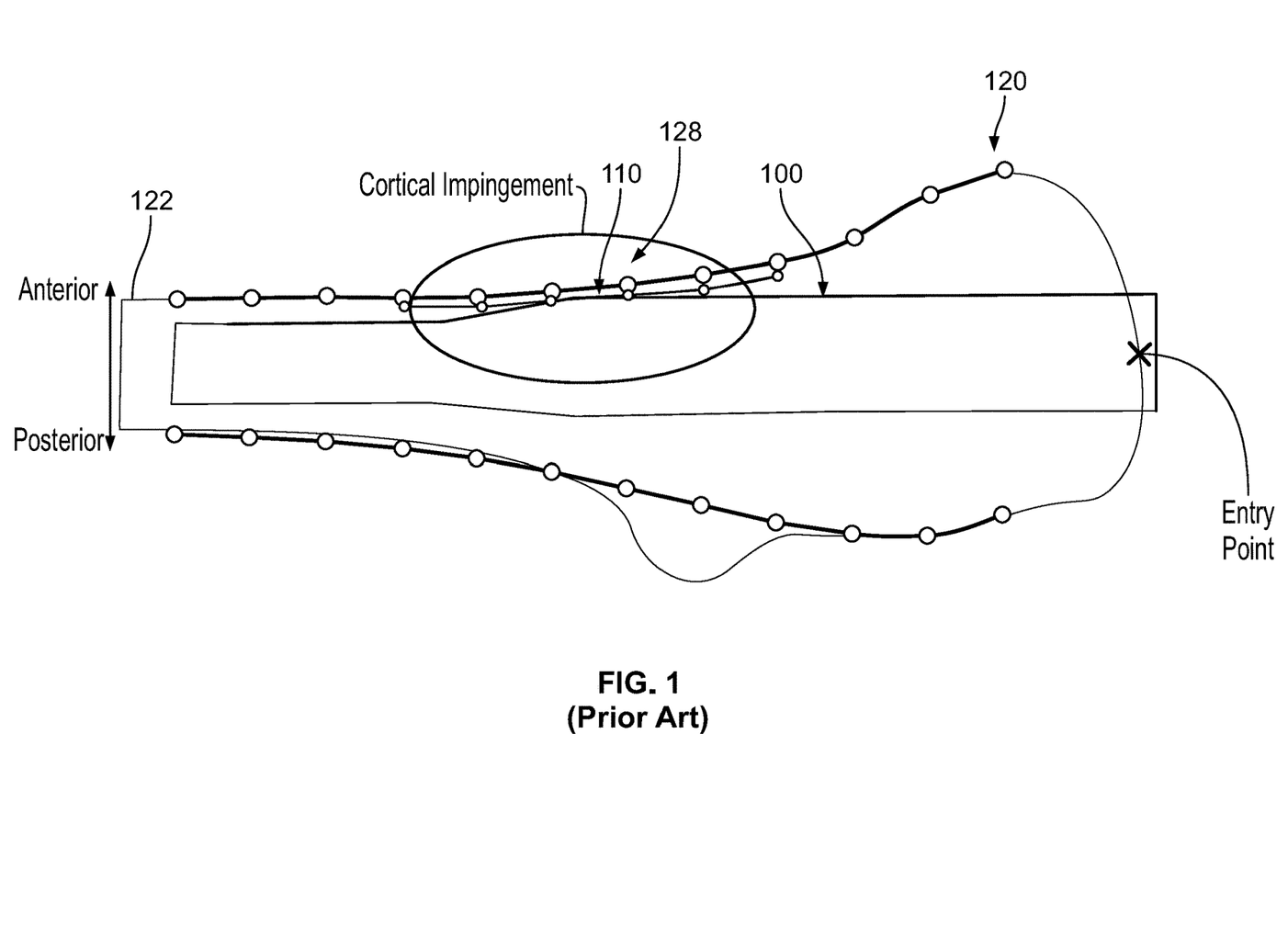
FIG. 1 is a schematic representation of a prior art femoral nail implanted in a proximal end of a femur.

FIG. 1 depicts an exemplary prior art femoral nail 100 implanted within a femur, such as the femur in FIG. 10, in an antegrade manner. As shown, the construction of femoral nail 100 is such that it has a portion 110 that impinges on the anterior cortex of the femur at transitional bend 128 between femoral shaft 122 and proximal femur 120. Such impingement may be caused by an underestimation of the curvature of the femur and, as illustrated in FIG. 1, may occur at transitional bend 128 which is a location at or near the transition or necking down of the proximal femur 120 to the femoral shaft 122. This can result in fracturing of the bone particularly as the nail 100 is impacted into the intramedullary canal of the femur. Moreover, even if fracture does not occur, the nail 100 may press against the cortex of the bone which can result in malalignment of both fracture fragments as well as the femoral nail 100 within the intramedullary canal as the nail may be constrained from coming to the desired seated position. This can lead to a non-anatomical bone shape when the bone fully heals, which can also lead to premature wear of articular cartilage in joint regions due to non-physiological alignments.

FIGS. 2-7 depict a femoral nail 10 according to an embodiment of the present disclosure. Femoral nail 10 configured for implantation in a left leg and generally includes a proximal section 20, a distal section 28 and an intermediate section therebetween. The intermediate section includes a first curved portion 22, a straight portion 24, and a second curved portion 26.

Figure 6:
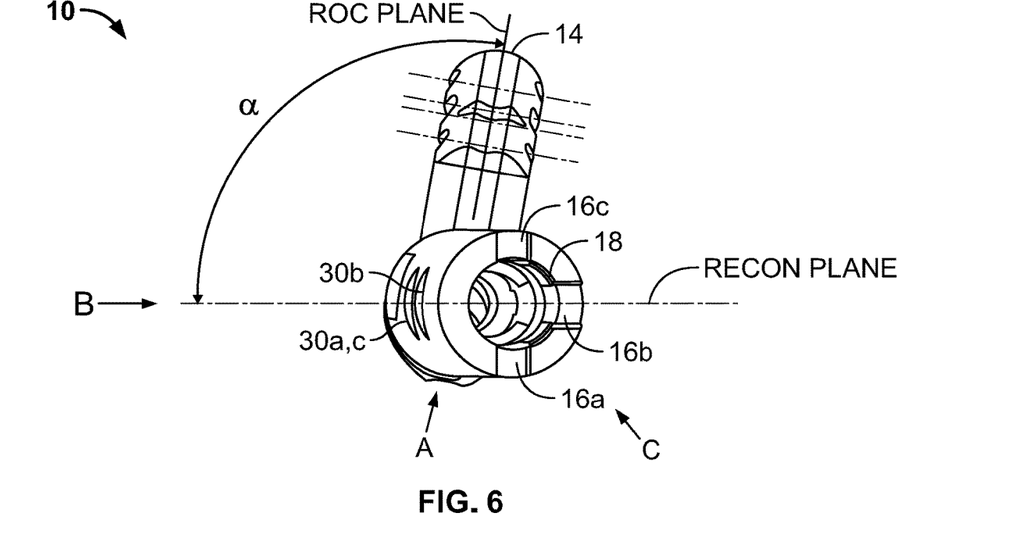
FIG. 6 is a top view of the femoral nail of FIG. 2.
Figure 7:
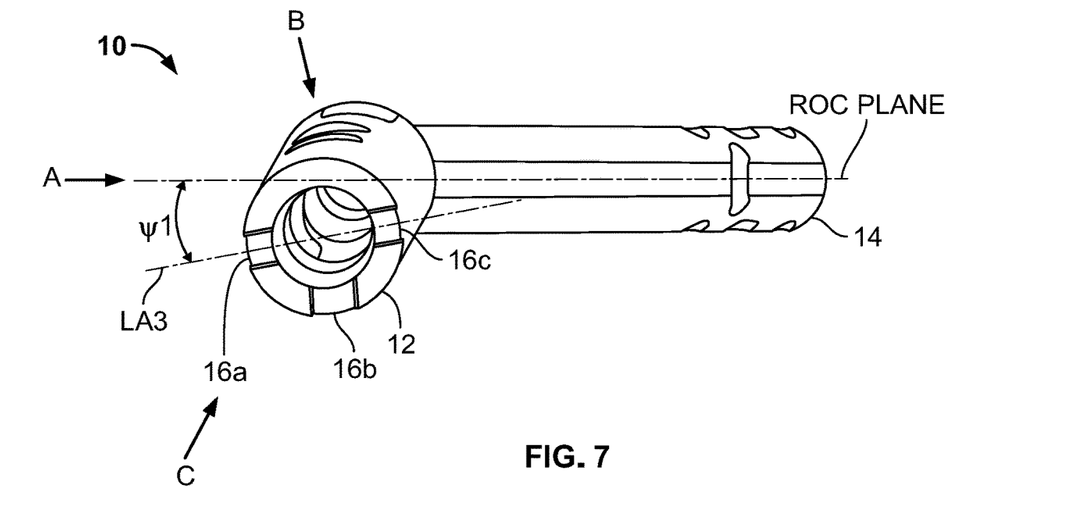
FIG. 7 is another top view of the femoral nail of FIG. 2.

In the particular embodiment depicted, proximal section 20 and distal section 28 are each substantially straight along their respective lengths. Distal section 28 terminates at a distal tip 14 which defines a distal end of nail 10. Proximal section 20 is generally cylindrical and defines a longitudinal axis LA1 that extends along its length. Proximal section 20 defines a proximal end 12 of nail 10 which is configured to be coupled to an alignment/aiming instrument, such as by a threaded connection. An example of an aiming instrument is disclosed in U.S. Pat. No. 6,039,739, the disclosure of which is incorporated herein by reference in its entirety. Also, as best shown in FIGS. 6 and 7, proximal end 12 includes a plurality of notches 16a-c positioned at predetermined intervals about the longitudinal axis LA1 of proximal section 20. Such notches 16a-c collectively form a clocking feature that helps properly orient femoral nail 10 respective to a femur during implantation and may assist in the connection between the alignment/aiming instrument and femoral nail 10.

Figure 3:
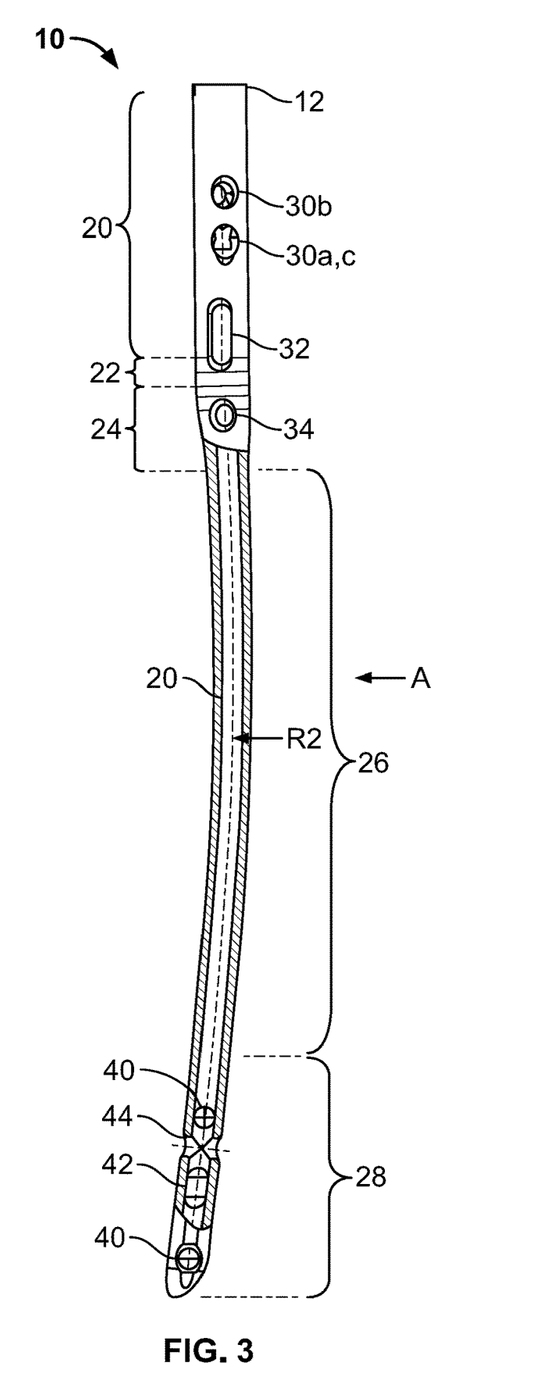
FIG. 3 is a partial cutaway side view of the femoral nail of FIG. 2 rotated 180 degrees.

Femoral nail 10 also includes a plurality of screw holes 30, 32, 34, 40, 42, 44 extending therethrough. As best shown in FIG. 3, nail 10 includes a first set of screw holes extending through proximal section 20 and the intermediate section, and a second set of screw holes extending through distal section 28. The first set of screw holes includes recon screw holes 30, a compression screw hole 32, and a static screw hole 34. Compression screw hole 32 is an elongate screw hole that defines an axis extending perpendicular to axis LA1 and allows for screw movement along axis LA1. Static screw hole 34 extends through intermediate section near proximal section 20 and also defines a screw hole axis that is perpendicular to axis LA1. However, static screw hole 34 constrains any screw inserted therein from movement along axis LA1.

Figure 4:
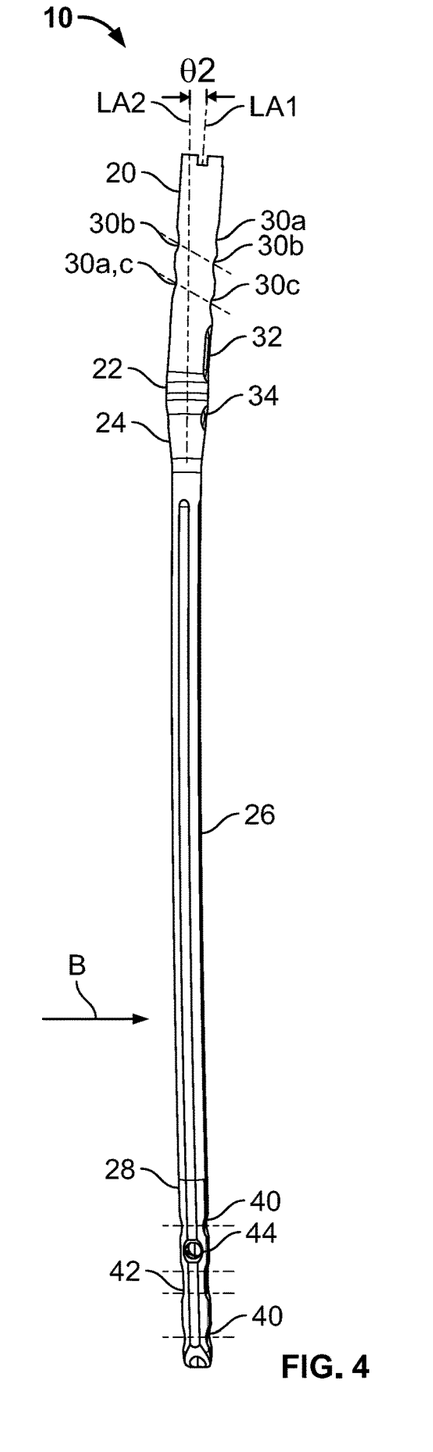
FIG. 4 is a front view of the femoral nail of FIG. 2 in a plane extending in a direction B.

The recon screw holes 30 form three openings 30a, 30b, and 30c at one side (i.e., lateral side) of nail and two openings 30b and 30a,c at an opposite side (i.e., medial side) of nail. In this regard, openings 30a and 30c converge to single opening 30a,c. Thus, a screw inserted through opening 30a or 30c extends through opening 30a,c at the opposite side of nail 10, while a screw inserted through opening 30b at one side of nail 10 extends through opening 30b at the opposite side of nail 10. As shown in FIG. 4, the screw holes 30 that are defined by openings 30a, 30b, and 30a,c define axes that extend at an oblique angle relative to axis LA1 and lie in a plane extending in a direction B as indicated by the arrow B in the figure. Such plane is referred to herein as a second plane or reconstruction plane ("Recon Plane"). The axes defined by openings 30a, 30b, and 30a,c also extend toward a femoral head and femoral neck of a patient's femur when implanted therein for a recon mode of fixation. Screw holes 30, 32, and 34 provide for multiple modes of fixation, such as the recon mode of fixation just mentioned as well as several others not specifically described herein.

The second set of screw holes, which extend through the distal section of nail, include static screw holes 40, a compression screw hole 42, and a transverse screw hole 44. Static screw holes 40 and compression screw hole 42 each extend through distal section 28 and define screw hole axes that are perpendicular to a longitudinal axis of distal section 28 and lie within the Recon Plane, as best shown in FIG. 4. Transverse screw hole 44 extends through distal portion 28 transverse to screw holes 40a-b and 44 and has an axis that is perpendicular to the longitudinal axis of distal section and lies within a plane which itself extends in a direction A, as shown in FIG. 3. Such plane is referred to herein as a first plane or radius of center plane ("ROC Plane"), as is described in more detail below. Also, transverse screw hole 44 is situated between static screw holes 40 along with compression screw hole 42.

In addition to the screw holes mentioned above, a bore 20 extends through proximal end 12 of nail 10 along its length and through distal tip 14. Proximal section 20 is internally threaded along a portion of the length of bore 20 adjacent the proximal end 12. Such internal threading is configured to mate with an alignment/aiming instrument and set-screw or cap, for example.

As mentioned above, the intermediate section includes a first curved or bent portion 22, a second curved or bent portion 26, and a straight portion 24. As depicted, first curved portion 22 extends distally from proximal section 20, second curved portion 26 extends proximally from distal section 28, and straight portion 24 is positioned between first and second curved portions 22, 26. Second curved portion 26 has a radius of curvature R2 of about 500 to 1500 mm which has been determined to conform to the anterior femoral bow of 95% of the patient population based on a diversified population analysis using a central database that contains geometric data of human bones. Second curved portion 26 is curved or bent in the first plane that extends in a direction A (indicated by arrow A in FIGS. 2 and 3). Hence, the first plane is referred to as the ROC Plane as mentioned above. In the particular embodiment depicted, second curved portion 26 is curved/bent in only the ROC Plane. However, it is contemplated that second curved portion 26 may be curved/bent in other planes transverse to the ROC Plane as desired to match a patient(s) anatomy.

Straight portion 24 is positioned between first and second curved portions 22, 26 and tapers from first curved portion 22 toward second curved portion 26 as this portion of nail 10 is intended to reside in the transition region between the metaphysis and diaphysis of the proximal femur. Straight portion 24 also defines a longitudinal axis LA2 extending along its length.

Figure 2:
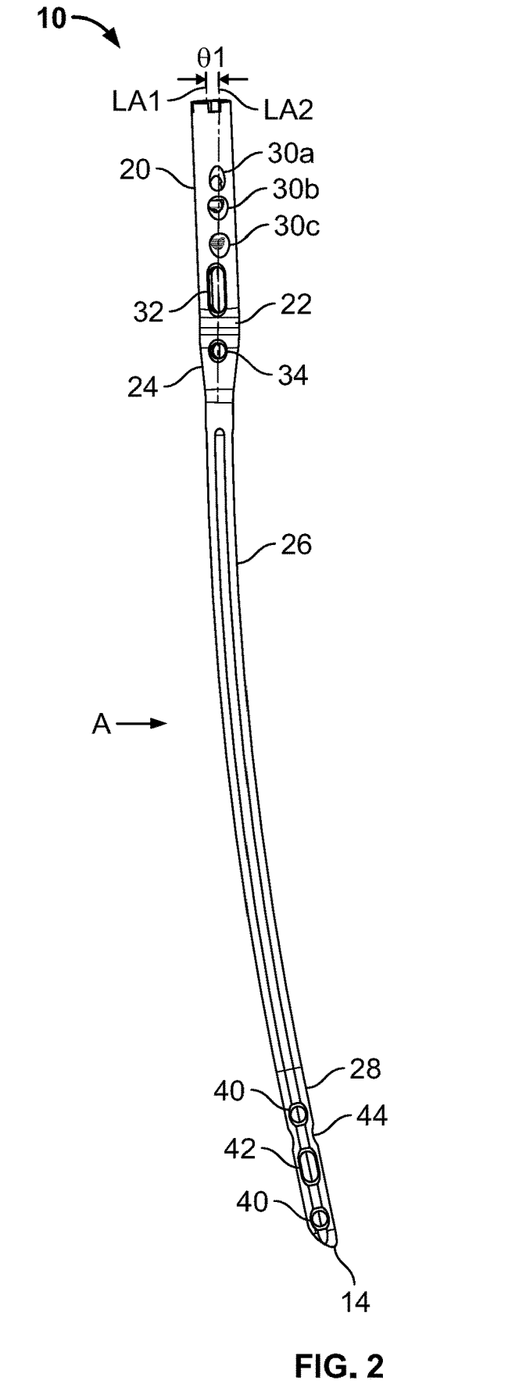
FIG. 2 is a side view of a femoral nail in a plane extending in a direction A.
Figure 5:
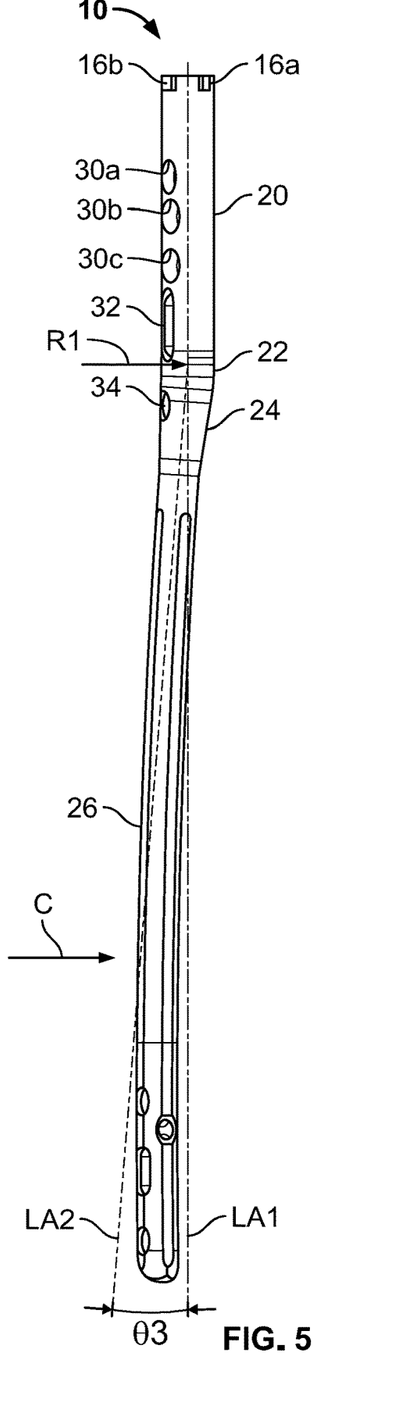
FIG. 5 is a rear view of the femoral nail of FIG. 2 in a plane extending in a direction C.

First curved portion 22 is shorter in length than second curved portion 26 and has a first radius of curvature R1 of about 30 to 50 mm as depicted in FIG. 5. In addition, first curved portion 22 is curved/bent in three separate, intersecting planes. More specifically, first curved portion 22 is curved/bent in the first plane or ROC Plane, as shown in FIGS. 2 and 3. First curved portion 22 is also curved/bent in a second plane or Recon plane that extends in a direction B, as depicted in FIG. 4. Moreover, first curved portion 22 is curved/bent in a third plane that extends in a direction C, as best shown in FIG. 5. The bends/curves in each of these planes define a radius of curvature of the first curved portion 22. Radius of curvature R1, which is mentioned above, lies in the third plane.

The bends of first curved portion 22 in each of the first, second, and third planes has the effect of orienting longitudinal axis LA2 of straight portion 24 relative to longitudinal axis LA1 of proximal section 20 at first, second, and third angles $\theta 1$, $\theta 2$, and $\theta 3$ within those respective planes. In other words, due to the multi-planar curvature of first curved portion 22, axis LA2 is angled relative to axis LA1 in the ROC Plane by a first bend angle $\theta 1$, in the Recon Plane by as second bend angle $\theta 2$, and in a Resultant Bend Plane by a third bend angle $\theta 3$, as shows in FIGS. 2, 4, and 5, respectively. Moreover, in the embodiment depicted, bend angles $\theta 1$, $\theta 2$, and $\theta 3$ differ in magnitude. However, it is contemplated that bend angles $\theta 1$, $\theta 2$, and $\theta 3$ may be equal in each of the three planes. Where bend angles differ, third bend angle $\theta 3$ is a resultant of the first and second bend angles $\theta 1$ and $\theta 2$. In this regard, the magnitude of $\theta 3$ and the orientation of the Resultant Bend Plane relative to the other planes are a function of $\theta 1$ and $\theta 2$ and the angular orientation between the ROC Plane and Recon Plane in which such first and second bends respectively lie. As an example, in the depicted embodiment, first bend angle $\theta 1$ is preferably 3 degrees in the ROC Plane, and second bend angle θ2 is preferably 4 degrees in the Recon Plane where the ROC Plane and Recon Planes are oriented at an oblique angle 1a which is preferably 100 degrees, as best shown in FIG. 6. Thus, in this example, third bend angle is about 4.5 degrees and Resultant Bend Plane is oriented about 59 degrees relative to ROC Plane and 41 degrees relative to Recon Plane It should be understood that while bend θ1, θ2, and θ3 are preferably and respectively 3, 4, and 4.5 degrees and angle α is preferably 100 degrees, these angles may differ. As such, angle α may be between 80 and 120 degrees, first bend angle θ1 may be between 1.5 and 4.5 degrees, second bend angle θ2 may be between 3 and 6 degrees, and third bend angle θ3 may be between 3 and 8 degrees. Such angles have been determined to suitably fit 95% of the patient population without the femoral cortex impingement described above based on a database analysis of a diverse population of bones.

Figure 8:
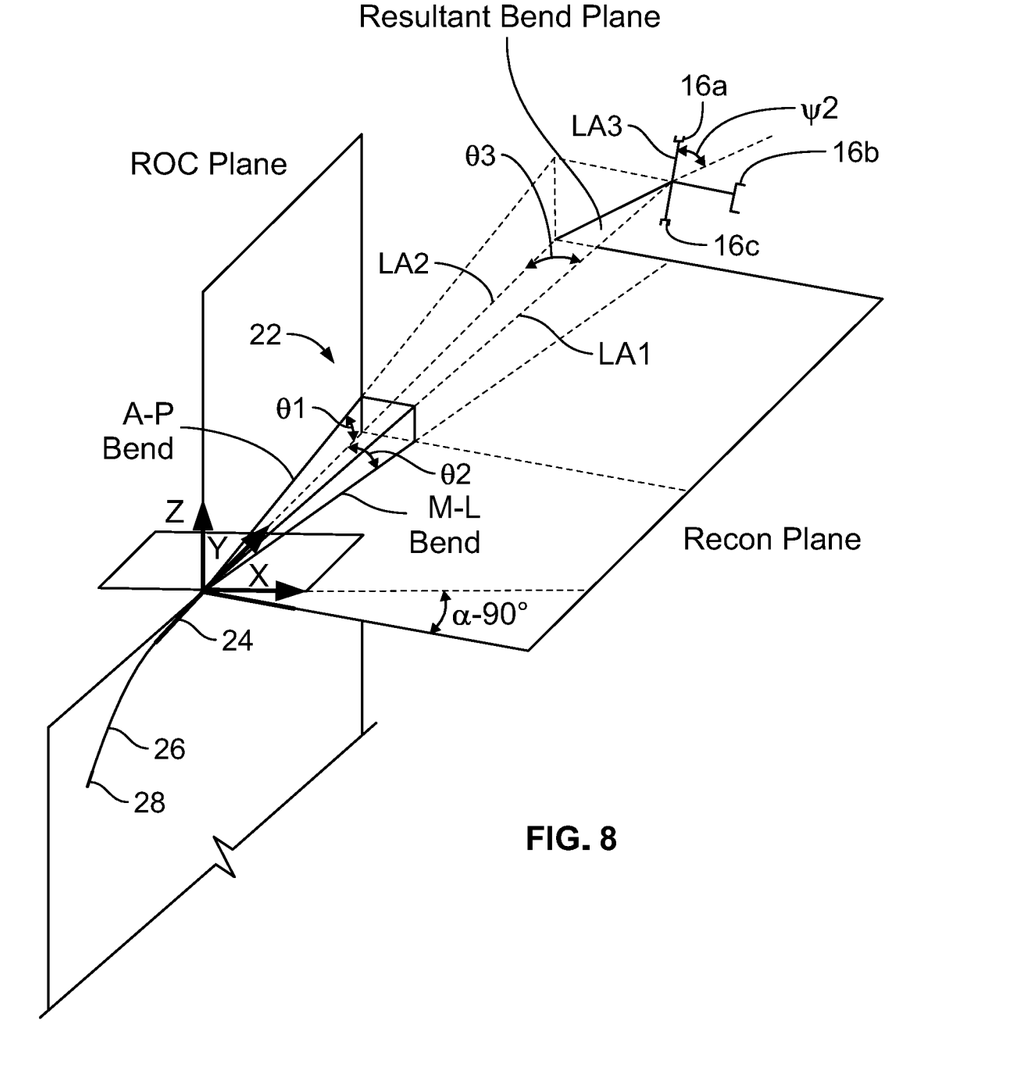
FIG. 8 is a schematic representation of the femoral nail of FIG. 2 in a Cartesian coordinate system.

FIG. 8 schematically illustrates the above described multi-planar bends/curves of first curved portion to help visualize the bends and how such bends are related to other structural features of nail 10, such as proximal notches 16a-c. As shown, first curved portion 22 bends in the ROC Plane at bend angle θ1 from axis LA2 of straight portion 24. First curved portion 22 also bends in the Recon Plane from axis LA2 at bend angle θ2. This results in axis LA1 of proximal section 20 being angled relative to axis LA2 of straight section by an angle θ3 in the Resultant Bend Plane. Also, as can be seen, a Cartesian coordinate system is established such that the z-axis extends generally in an anterior-posterior direction, the x-axis extends generally in a lateral-medial direction, and the y-axis extends generally in a superior-inferior direction with the origin being located at the interface between first curved portion 22 and straight portion 24. The origin may also be located anywhere from about 10% to 40% of the length of nail 10 measured from a proximal end thereof. The y-axis coincides with longitudinal axis LA2 of straight section 24 and also defines the intersection between the ROC Plane, Recon Plane, and Resultant Bend Plane. Thus, for the left legged nail 10 described herein, the multi-planar bend has the effect of orienting proximal section 20 anteriorly and medially relative to straight portion 24. In this regard, proximal section 20 slopes posteriorly in the superior to inferior direction which results in a canting away of nail 10 from an anterior cortex of a femur at the common impingement area as illustrated in FIG. 1. It also aligns proximal section 20 and intermediate section with the natural lateral-medial curve of a femur. It should be understood that these bends are mirrored for a right-legged femoral nail.

As also shown in FIG. 8, ROC Plane is oriented relative to the Recon Plane in the Cartesian coordinate system by the obtuse angle α. Thus, the Recon Plane is oriented relative to the x-plane within the Cartesian coordinate system by α−90°. Thus, where angle α is 100 degrees, Recon Plane is angled relative to the x-plane by 10 degrees. This offset of the Recon Plane relative to the x-plane helps form the bend in the Resultant Bend Plane and happens to also be equal to the angle ψ1. ψ1 is the angle formed between the ROC Plane and a longitudinal axis LA3 which bisects notches 16a and 16c, as shown in FIG. 7. In addition, an angle ψ2 is formed between axis LA3 and Resultant Bend Plane. Thus, the angle between the ROC Plane and the Resultant Bend plane is equal to the sum of ψ1 and ψ2. Therefore, in the example provided above where α is 100 degrees, ψ1 is 10 degrees, and ψ2 is 49 degrees, the angle between the ROC Plane and Resultant Bend Plane is 59 degrees.

Figure 9:
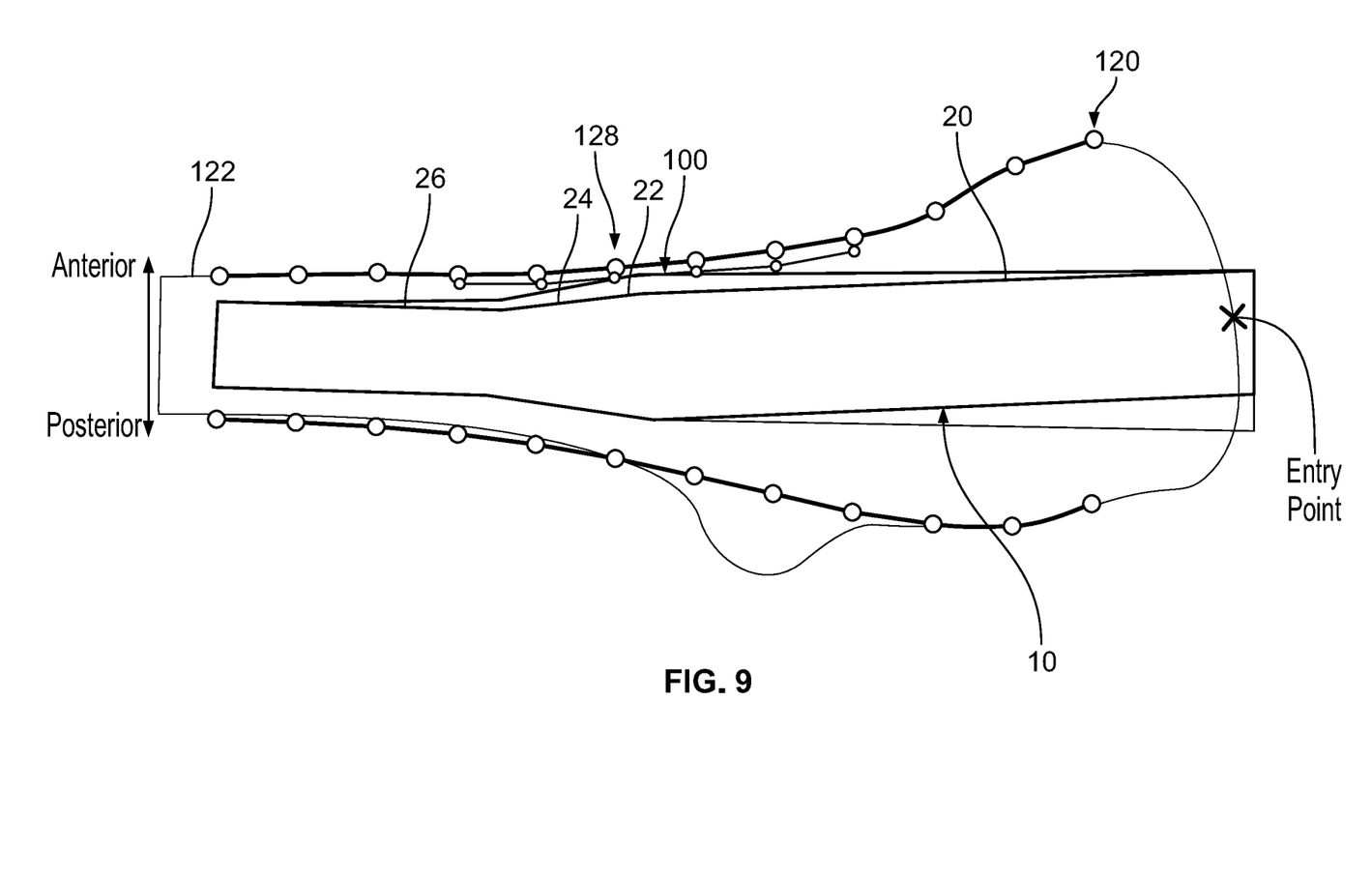
FIG. 9 is a schematic representation of the femoral nail of FIG. 2 overlaying the prior art femoral nail and femur of FIG. 1.

FIG. 9 illustrates the above described effect on femoral cortex impingement of the multi-planar bends. As shown, nail 10 overlays prior art nail 100 and, as a result of bends of first curve portion 22, nail 10 cants away from the anterior cortex of the femur at the common impingement zone of prior art nail 100 thereby reducing the possibility of femoral cortex impingement.

Femoral nail 10 may have alternative constructions to that described above while remaining within the scope of the invention. For example, in one embodiment, femoral nail 10 may not include a straight distal end 28. Instead, second curved portion 24 may define the distal end 14 of nail 10. In this regard, second curved portion 26 may curve about its center of curvature from straight portion 24 all the way to distal tip 14 of femoral nail 10. Alternatively, distal section 28 may itself be curved/bent in one or more planes so that it has a different radius of curvature than that of second curved portion 26. In addition, proximal section 20 may also be curved/bent along its length in one or more planes.

In another embodiment, nail 10 may not include a straight portion 24 within the intermediate section. In such embodiment, second curved portion 26 may then be positioned adjacent first curved portion 22 and may extend distally therefrom. Thus, intermediate section may include a first curved portion 22 with a first radius of curvature R1 that defines bends in three separate planes, and a second curved portion 26 extending distally from the first curved portion 22 and curved/bent about a center of curvature in at least one plane. Although, in this embodiment, the straight portion 24 may be absent, the advantages described above with regard to nail 10 may still be present.

Moreover, it should be understood that while it is described herein that first curved portion 22 and second curved portion 26 are each curved/bent in the ROC Plane, this may not be the case in every embodiment. It is possible that first curved portion 22 may be curved bent in three separate planes where none of these planes are coincident with the plane in which second curved portion 26 is curved.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A femoral nail comprising a proximal portion configured to engage a driving tool for driving the femoral nail into a femur; a distal portion remote from the proximal portion; and an intermediate portion disposed between the proximal portion and distal portion, the intermediate portion having a first bent section defined by a third bend angle of a non-zero radius of curvature in a third plane, the third bend angle being a resultant of a first bend angle within a first plane and a second bend angle within a second plane, the first and second planes intersecting at an oblique angle relative to each other, a reference plane orthogonal to the first plane extending between the second and third planes.

2. The femoral nail of claim 1, wherein the distal portion is substantially straight and includes a plurality of through-holes extending through the distal portion in a direction transverse to a distal end axis.

3. The femoral nail of claim 1, wherein the first plane is greater than 80 degrees and smaller than 120 degrees relative to the second plane.

4. The femoral nail of claim 3, wherein the first plane is 100 degrees relative to the second plane.

5. The femoral nail of claim 3, wherein the first plane is coplanar with an anterior-posterior plane, and the reference plane is a medial-lateral plane that is orthogonal to the anterior-posterior plane and extends substantially in a medial-lateral direction.

6. The femoral nail of claim 1, wherein the first bend angle is 3 degrees relative to a longitudinal axis defined by an intersection between the first and second planes and the second bend angle is 4 degrees relative to the longitudinal axis.

7. The femoral nail of claim 6, wherein the third bend angle is greater than 4 degrees relative to the longitudinal axis.

8. The femoral nail of claim 1, wherein the proximal portion of the femoral nail includes a plurality of through-holes extending therethrough, at least a first and second through-hole of the plurality of through-holes having respective first and second through-hole axes that lay in the second plane.

9. The femoral nail of claim 1, wherein the proximal portion includes a rotational alignment characteristic for indicating a rotational alignment of the femoral nail relative to a femur, the rotational alignment characteristic being rotationally offset from the third plane by an acute angle.

10. The femoral nail of claim 9, wherein the acute angle is less than 50 degrees.

11. The femoral nail of claim 10, wherein the rotational alignment characteristic is an engagement notch configured to engage the driving tool.

12. The femoral nail of claim 1, wherein the third plane intersects the second plane at an acute angle less than 50 degrees.

13. The femoral nail of claim 1, wherein curvatures of each of the bend angles begin their respective curvatures at a common origin.

14. The femoral nail of claim 1, wherein the intermediate portion includes a second bent section disposed between the distal portion and first bent section.

15. The femoral nail of claim 14, wherein the intermediate portion includes a straight section disposed between the first and second bent sections.

16. The femoral nail of claim 14, wherein the second bent section has a non-zero radius of curvature in the first plane.

17. The femoral nail of claim 1, wherein the distal portion defines a distal tip of the femoral nail, and the first bent section bends in an anterior direction away from the distal tip.

18. A femoral nail comprising a proximal section having a longitudinal axis extending along a length thereof; a distal section remote from the proximal section; and an intermediate section disposed between the proximal section and the distal section and having a straight portion and first bent portion, the first bent portion being disposed between the straight portion and the proximal section, wherein a longitudinal axis of the straight portion is oriented relative to a longitudinal axis of the proximal section by first, second, and third angles within respective first, second, and third planes, and wherein the first, second, and third angles differ from one another, wherein the intermediate section further includes a second bent portion disposed between the straight portion and the distal section, the second bent portion being bent in the first plane, wherein the first and the second planes intersect at an oblique angle.

19. A femoral nail comprising a first section having a first screw hole extending through a sidewall thereof and defining a screw hole axis configured to extend toward a femoral head when the femoral nail is implanted within a femur, the screw hole axis lying in a first plane; and a second section extending from the first section and having first and second curved portions, the first curved portion being positioned closer to the first section than the second curved portion, the second curved portion having a proximal-distal length greater than that of the first curved portion, the second curved portion being curved in a second plane that intersects the first plane at an oblique angle, and the first curved portion being curved in a third plane, the second and third planes each being different from the first plane.

20. The femoral nail of claim 19, wherein the first and second plane are oriented relative to each other at an obtuse angle, and the third plane is disposed between the first and second planes and is oriented relative to the second plane at an acute angle.

* * * * *